United States Patent [19]

Conner

[11] Patent Number: 4,680,144
[45] Date of Patent: Jul. 14, 1987

[54] BENZENE SULFONATE QUATERNARY AMMONIUM SALTS OF ORGANIC SUNSCREEN CARBOXYLIC ACIDS

[75] Inventor: Donald E. Conner, Clifton, N.J.

[73] Assignee: Mallinckrodt, Inc., St. Louis, Mo.

[21] Appl. No.: 924,340

[22] Filed: Oct. 29, 1986

Related U.S. Application Data

[63] Continuation-in-part of Ser. No. 623,206, Jun. 21, 1984, abandoned.

[51] Int. Cl.$^4$ ............ C07C 87/68; C07C 95/08; A61K 7/06; A01K 7/42
[52] U.S. Cl. ............ 260/501.15; 424/47; 424/59; 424/60; 424/70
[58] Field of Search ............ 260/501.15; 424/59, 424/60, 47, 70

[56] References Cited

U.S. PATENT DOCUMENTS

| | | | |
|---|---|---|---|
| 3,383,410 | 5/1968 | Johnson et al. | 260/501.15 |
| 4,012,398 | 3/1977 | Conner et al. | 424/60 |
| 4,061,730 | 12/1977 | Kalopissis et al. | 424/59 |
| 4,104,368 | 8/1978 | Lada et al. | 424/60 |
| 4,256,664 | 3/1981 | Epstein et al. | 564/177 |
| 4,457,911 | 9/1984 | Conner et al. | 424/59 |

FOREIGN PATENT DOCUMENTS 2504530 10/1982 France ............ 424/60

OTHER PUBLICATIONS

*The Merck Index,* 8th, 1968, p. 373, "Dimethocaine.

*Primary Examiner*—Glennon H. Hollrah
*Assistant Examiner*—Raymond Covington
*Attorney, Agent, or Firm*—L. Chasan; L. Goodwin; R. Klostermann

[57] ABSTRACT

Compositions of benzene sulfonate quaternary ammonium salts of organic sunscreen carboxylic acids have substantially for human hair and protect it from the undesirable effects of sunlight.

4 Claims, No Drawings

BENZENE SULFONATE QUATERNARY AMMONIUM SALTS OF ORGANIC SUNSCREEN CARBOXYLIC ACIDS

CROSS REFERENCE TO RELATED APPLICATIONS

This application is a continuation-in-part of Ser. No. 623,206 filed June 21, 1984, now abondoned.

FIELD OF THE INVENTION

It has become increasingly apparent that UV light, in addition to having detrimental effects on skin, can also adversely affect human hair. Excessive exposure of hair to UV light causes brittleness, and in the case of dyed hair, discoloration, and loss of color fidelity.

Organic sunscreens are generally unsuitable for application to human hair because of inadequate substantivity. Thus, they tend to rinse out of the hair and are accordingly ineffective.

Prior art attempts to remedy these shortcomings have not proved effective, or improved substantivity.

PRIOR ART

U.S. Pat. No. 3,878,229 teaches the preparation of various sunscreen complexes, differing in structure from quaternary tosyl sulfonate salts. U.S. Pat. No. 4,256,664 discloses halogen containing quats from amides of salicyclic acids, but no tosylates. U.S. Pat. No. 4,061,730 discloses a tosylate quat of benzylidene camphor. U.S. Pat. No. 4,104,368 discloses cationic, anionic complexes formed by reacting an alkali metal salt of a sunscreen. French Pat. No. 2,504,530 uses alkyl halides in the quaternization step.

SUMMARY OF THE INVENTION

It has now been found that benzene sulfonate quaternary ammonium salt of organic sunscreen carboxylic acids, believed to be novel chemicals, have very surprising substantivity for hair, and thus substantially protect it from the undesirable effects of sunlight.

DETAILED DESCRIPTION OF THE INVENTORY

The quaternary salts of this invention correspond to the formula:

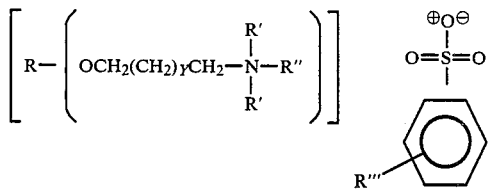

wherein the RCO moiety is selected from the group consisting of p-amino benzoic acid, p-dimethyl amino benzoic acid, p-methoxy cinnamic acid, p-methoxy benzal malonic acid, and cinnamal malonic acid; R' is an alkyl group having from 1 to 2 carbon atoms; R'' is an alkyl group having from 10 to 20 carbon atoms; R''' is selected from the group consisting of H and $CH_3$; and Y is an integer of 0 to 1.

Particularly preferred are those compounds where the RCO moiety is p-dimethyl amino benzoic acid, p-methoxy cinnamic acid, p-methoxy benzal malonic acid, or cinnamal malonic acid; where R'' is $C_{16-18}$; and R''' is $CH_3$ and in the para position.

To obtain the derivative containing the necessary tertiary nitrogen various conventional techniques can be employed e.g. transesterification (of the methylester with a tert amino alcohol), reaction of an acid chloride with a tert amino alcohol using pyridine or triethylamine as solvent and catalyst; esterification of nitro benzoic acid with tert amino alcohols or amines, followed by reduction, or reductive alkylation; etc., e.g., see U.S. Pat. No. 4,012,398.

Then the derivative is quaternized by reaction, with an ester of the sulfonic acid. The reaction is carried out conveniently in an isopropanol or toluene solution, which is heated to 75°–120° for about 3 to 6 hours.

The compounds of this invention are formulated into otherwise conventional compositions adapted for application to human hair. Thus they can be applied in an effective amount in cosmetic carriers known to the trade e.g. shampoos. sprays, and other specialty products. Concentrations of about 1 to 6 wt.% in the composition are conveniently employed.

The compounds of this inventory provide versatility in formulation since different compounds have different solubilities in water and organic solvents, and have peak absorptions at different pHs.

This invention, product work up, and properties of the materials will be better understood by reference to the following examples.

EXAMPLE 1

Cetyl Stearyl Sulfonate Quaternary of 2-dimethylamino Ethyl p-dimethylamino Benzoate Charge:
- 224 g (1 mole) 2-dimethylamino ethyl-p-dimethylamino benzoate
- 442 g (1 combining wt.) cetyl/stearyl toluene sulfonate
- 600 g Toluene The above materials were heated under reflux for 6 hours. At the end of this period the mixture was cooled to room temperature and the solid filtered off. After recrystallization twice from acetone (toluene can also be used) the solids were as charged. A yield of 565 grams (84.8% of theory) was obtained having a m.p. of 153°–157° C. and an alkali number of 0.13.

Using the same procedure, the following compounds were prepared:

EXAMPLE 2

Lauryl p-toluene Sulfonate Quaternary of 2-dimethyl Amino Ethyl p-dimethyl Amino Benzoate Off white solid was obtained in 87% yield—Alkali 2.6 and a M.P. of 133°–137° C.

EXAMPLE 3

Cetyl/Stearyl p-toluene Sulfonate Quaternary of 2-dimethyl Amino Ethyl p-methoxy Cinnamate Compound obtained in 80% yield—melting point 139°–144° C. and an alkali number of 0.0.

EXAMPLE 4

Cetyl/Stearyl p-toluene Sulfonate Quaternary of 2-dimethyl Amino Ethyl p-dimethyl Amino Benzoate Obtained in an 88% yield, melting point 106°–147° C., and alkali number of 1.6.

EXAMPLE 5

Di-Cetyl/Stearyl p-toluene Sulfonate Quaternary of di(2-dimethyl amino ethyl)p-methoxy Benzal Malonate A yield of 89% was obtained, the compound had an alkali number of 3.5, and was a very viscous liquid.

EXAMPLE 6

In order to demonstrate the substantivity and effectiveness of these compounds in prevention of the fading of dyed human hair, the following test programs were carried out on the compounds of Examples 3–5.

The test samples were prepared by taking 1 gram of dyed human hair in a 3% solution or dispersion of each of the test compounds. After standing for 1 hour the hair was removed from the solution, one half was air dried, and the other half was rinsed for 5 minutes in tap water and then dried.

All test samples were irradiated with a Hanovia Ultra Violet Lamp containing a Corex D filter. The control was 2-ethylhexyl p-dimethylaminobenzoate. It was found that at 45 hours, fading in the control occurred with no fading of the treated sample.

The rinsed samples also retained $\frac{1}{2}$ to $\frac{3}{4}$ of their fade resistance.

EXAMPLE 7

Benzylidene camphor; dodecyl p-toluene sulfonate; and 4-[(2-oxo-3-bornylidene)methyl]-phenyl dimethyl dodecylammonium paratoluene sulfonate were synthesized, the latter by the method of U.S. Pat. No. 4,061,730 as well as others. The benzylidene camphor, (A); 4-[(2-oxo-3-bornylidene)methyl]-phenyl dimethyl dodecylammonium paratoluene sulfonate, (B); and the cetyl stearyl sulfonate quaternary of 2-di-methylamino ethyl p-dimethylamino benzoate, (C); (ex. 1); were tested according to the following procedure for sunscreen efficacy:

The effectivness of a sunscreening agent is determined by dividing the absorbance at the maximum peak between 300 and 320 n.m. by the concentration in grams per liter. This is known as the "K" value of a sunscreening agent. The higher the "K" value, the better the sunscreening ability and the lower the amount of material needed for protection from erythemal rays of the sun. In other words, from the "K" value the amount of sunscreening agent necessary for protection from the sun ultraviolet radiation can be determined and used in any cosmetically acceptable base preparation.

Reproduced below are the data obtained:

| K Values | |
| --- | --- |
| Compound A | 0.08 |
| | 0.24 |
| Compound B | 0.02 |
| | 0.03 |
| | 0.04 |
| Compound C | 48 |

These data demonstrate that Compounds A and B are not effective sunscreens, and that the efficacy of the claimed compounds are infinitely superior.

Other materials of this invention work similarly. This work clearly demonstrates that these compounds are very good U.V. absorbers and that they have good substantivity for human hair, enough to prevent fading, superior to an ordinary comparable sunscreen.

Additional compounds for similar utility can be prepared utilizing other organic sunscreens containing a carboxylic group.

The advantages of this invention will be apparent to those skilled in the art. Improved highly effective novel materials are provided having substantivity for hair which also impart protection against harmful sunlight.

It will be understood that this invention is not limited to the specific examples which have been offered as particular embodiments, and that modifications can be made without departing from the spirit thereof.

What is claimed is:

1. As a novel composition of matter, a benzene sulfonate quaternary salt of an organic sunscreen carboxylic acid corresponding to the formula:

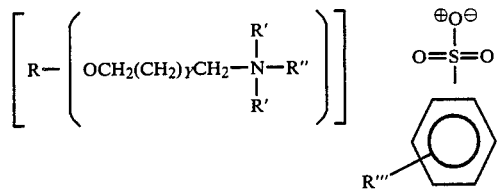

wherein the R is an acyl derived from the group consisting of p-amino benzoyl, p-dimethyl amino benzoyl, p-methoxy cinnamoyl, p-methoxy benzal, and cinnamal malonoyl; R' is an alkyl group having from 1 to 2 carbon atoms; R" is an alkyl group having from 10 to 20 carbon atoms; R''' is selected from the group consisting of H and CH₃; and Y is an integer of 0 to 1.

2. The composition of claim 1 selected from the group consisting of cetyl/stearyl p-toluene sulfonate quaternary of 2-dimethyl amino ethyl p-dimethyl amino benzoate; cetyl/stearyl p-toluene sulfonate quaternary of 2-dimethyl amino ethyl p-methoxy cinnamate; and di-cetyl stearyl p-toluene sulfonate quaternary of di-(2-dimethyl amino ethyl)p-methoxy benzal malonate.

3. A composition adapted for application to human hair comprising a cosmetic carrier containing an effective amount, sufficient to provide substantial protection from the effects of sunlight of a benzene sulfonate quaternary salt of an organic sunscreen carboxylic acid corresponding to the formula

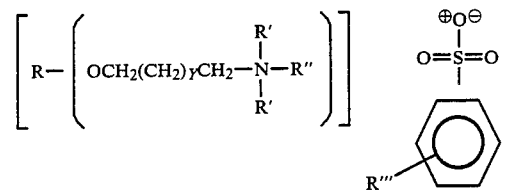

wherein the R is an acyl derived from the group consisting of p-amino benzoyl, p-dimethyl amino benzoyl, p-methoxy cinnamoyl, p-methoxy benzal malonoyl, and cinnamal malonoyl; R' is an alkyl group having from 1 to 2 carbon atoms; R" is an alkyl group having from 10 to 20 carbon atoms; R''' is selected from the group consisting of H and CH₃; and Y is an integer of 0 to 1.

4. The composition of claim 3 in which the salt is selected from the group consisting of cetyl-stearyl p-toluene sulfonate quaternary of 2-dimethyl amino ethyl p-dimethyl amino benzoate; cetyl/stearyl p-toluene sulfonate quaternary of 2-dimethyl amino ethyl p-methoxy cinnamate; and di-cetyl stearyl p-toluene sulfonate quaternary of di(2-dimethyl amino ethyl)p-methoxy benzal malonate.

* * * * *